United States Patent [19]
Atlas

[11] Patent Number: 5,498,407
[45] Date of Patent: Mar. 12, 1996

[54] POLY(2-HYDROXYETHYL METHACRYLATE) AND ALL COPOLYMERS OF POLY-HEMA FIBERS AND COSMETIC COMPOSITIONS CONTAINING SAME

[76] Inventor: Sheldon M. Atlas, 211 Central Park West, New York, N.Y. 10024

[21] Appl. No.: 328,091

[22] Filed: Oct. 24, 1994

[51] Int. Cl.$^6$ ............................ A61K 7/035; A61K 7/04; A61K 7/027
[52] U.S. Cl. .................. 424/70.7; 424/61; 424/64; 424/78.31; 424/78.32; 424/401; 424/DIG. 5; 514/844; 514/845
[58] Field of Search ............................ 424/61, 401, 70.7, 424/64, 78.31, 78.32, DIG. 5; 514/844, 845

[56] References Cited

U.S. PATENT DOCUMENTS

| | | | |
|---|---|---|---|
| 4,484,926 | 11/1984 | Atlas | 8/115.5 |
| 4,814,131 | 3/1989 | Atlas | 264/147 |

*Primary Examiner*—Jyothsan Venkat

[57] ABSTRACT

Hydrogels are polymers that swell in water and are hydrophilic. The degree and nature of cross linking and the crystallinity of the polymer are responsible for its properties in the swollen state, and the degree to which it imbibes water without the loss of shape is important in many natural hydrogel. Some natural hydrogels are used in the textile industry, pulp and paper production, artificial silk, cellulosic membranes, and biomedical applications. Synthetic hydrogels are used in soft lenses, prosthetic materials and membranes for controlled drug delivery.

Poly-HEMA (poly 2 hydroxylthyl methacrylate) is the most widely used hydrogel. The properties of poly HEMA can be modified by cross linking to a certain degree but its hydrophilicity can be increased by the introduction of a second hydroxyl using various monomers. Also its strength will also improve by the addition of a comonomer. These copolymers yielding increase hydrophilicity and strength are exhibited in soft hydrogel films, flexible even in the dry state. Copolymers of HEMA have been utilized in drug delivery systems where the drug diffusion is controlled by the type and ratios of comonomers used together with certain cross linking agents. Comonomers with anionic fixed charges are incorporated in poly HEMA chains, e.g. Methacylic acid (MAA) and acrylic acid(AA). The gels formed containing MAA used in soft contact lenses absorb much more protein than any other gels. Homopolymer poly HEMA fibers and various copolymers of poly HEMA have been combined with standard cosmetic, skin, and nail formulations to provide excellent, enhanced properties to the human body.

5 Claims, No Drawings

POLY(2-HYDROXYETHYL METHACRYLATE) AND ALL COPOLYMERS OF POLY-HEMA FIBERS AND COSMETIC COMPOSITIONS CONTAINING SAME

Hydrogels are cross-link macromolecular networks swollen in water and other biological fluids. Since their discovery, polyHEMA (poly 2-hydroxyethyl methacrylate) and a wide range of hydrophilic polymers have been examined as potential candidates for replacement of soft tissue, tendons, muscles and other biomedical applications. More recently, hydrogels have become excellent carriers for release of drugs and active macromolecules in their equilibrium swollen state on or as dynamic swollen systems.

The biocompatability of hydrogels is attributed to their ability to simulate natural tissue due to their high water content and their special surface properties. Hydrogels, in addition, can be made more or less hydrophilic by copolymerization of two or more monomers. The disadvantage is their relatively low mechanical strength which can be overcome by either cross-linking or by crystallization.

It was unexpected and surprising to find the P-HEMA hydrogels fibers we have described are biocompatable, as with permanent body implants such as intraocular lenses, and can be appropriately combined with traditional cosmetic and other topically applied skin and nail preparations to provide excellent properties to the human skin and welfare never previously observed or achieved. This is due to the increased area created by size and shape of the HEMA polymeric or copolymeric fibers swelling capacities and controlled release rate creating a constant healthy equilibrium when applied to skin and nails.

I have previously described, U.S. Pat. No. 4,484,926, the incorporation specialty textile fibers which are fabricated from cross-linked high molecular weight hygroscopic polymers which specialty fibers are capable of absorbing large quantities of moisture without degradation of tensile strength and other fiber properties. This was accomplished by incorporating in a fabric at least about 1% by weight of a novel specialty fiber which is formed from a linear hygroscopic homopolymer having only carbon to carbon bonds in the polymer backbone with hydrophilic side chains in the repeating recurring units, the polymer being formed from a monomer selected from the group consisting of alpha, beta—ethylenically unsaturated aliphatic carboxylic acids, alpha, beta-ethylinically unsaturated aliphatic sulfonic acids, hydroxyalkyl esters of these aliphatic carboxylic and sulfonic acids, and glycidyl esters of these aliphatic carboxylic and sulfonic acids, such polymers having a molecular weight in the range from about 100,000 to about 500,000, a softening point in the range of from about 210° C. to about 245° C. and a glass transition temperature Tg above about 115° C. The homopolymers being cross-linked at a cross linking density in the range of one cross-linkage per from about 40 to about 100 repeating monomeric units of the homopolymer. These fibers are capable of absorbing up to about 40% by weight of the fiber of moisture without loss of mechanical strength and other textile properties.

The monomers cited, generally, have from 1 to 10 carbon atoms preferably 1 to 6 carbon atoms, can be used. Examples of the alpha, beta-unsaturated aliphatic carboxylic acids include crotonic acid, acrylic acid, methacrylic acid, ethacrylic acid, alphaisopropylidene acrylic acid, alpha-vinyl acrylic acid and the like. As examples of the ethylenically unsaturated aliphatic sulfonic acids, any of the foregoing carboxylic acids in which the carboxylic (—COOH) group is substituted by the sulfonic acid (—SO$_3$H) group can be used. Preferred examples of the olefinically unsaturated sulfonic acids include vinyl sulfonic acid, p-styrene sulfonic acid.

The hydroxyalkyl esters of these aliphatic carboxylic and sulfonic acid esters may have from 1 to 3 hydroxyl groups. Examples of the hydroxylalkyl esters include, for example, 2-hydroxyethylacrylate, 2-hydroxypropyl acrylate, 3-hydroxypropylacrylate, 4-hydroxyantyl-acrylate, 5-hydroxypentylacrylate, 2-hydroxylethylmethacrylate, 2-hydroxypropyl methacrylate, 3-hydroxypropylmethacrylate, 4-hydroxybutylmethacrylate and the hydroxy acrylate and hydroxymethacrylates of the corresponding sulfonic acids.

Examples of the hydroxyglycidyl esters of the aliphatic carboxylic and sulfonic acids are the hydroxyglycidyl esters of acrylic acid, crotonic acid, vinyl sulfonic acid, and p-styrene sulfonic acid.

I have also previously described U.S. Pat. No. 4,814,131 a process for the production of composite shaped articles having a hydrophobic component and a hydrophilic component. A stable blend of two polymer species is formed into a shaped article, such as a fiber or filament. The major component, A, of the polyblend is a linear high melting, crystalline hydrophobic polymer. The other minor component, B, is a linear non-crystalline hydrophilic polymer. Examples of polymer A, the predominant component are linear polyamides, linear polyester such as polyethylene terephthalate, polytetramethylene terephthalate, etc.; polyolefines, polyacrylanitriles, and other hydrophobic vinyl polymers.

Polymer B is the minor component and examples of suitable polymers include nylon 2, polyethylene oxide, polyhydroxyethylacrylate and—methacrylate and copolymers include poly(acrylonitrile) acrylamide; poly vinyl or vinylidene chloride) vinyl alcohol. Other U.S. Pat. Nos: 4,536,554; 4,443,515; 4,814,131; 4,430,458 list a number of monomers, polymers, copolymers etc. which can be utilized e.g. N-vinyl-2-pyrrolidone. Persons skilled in the art recognize a great number of homo -; co-; and ter-polymers which can be used.

However, these new and unexpected findings result in a network where it is unique to add a fiberous network to a skin or to a nail preparation that meters out a moisturizing effect and maintains an equilibrium.

In all the following examples the specification ranges are herein listed:

1. Wall thickness 5 microns±2 microns
2. I.D. 10 microns±5 microns
3. O.D. 20 microns±5 microns or as listed in the Claims solid fibers.

The percentage of fibers added range from 0.5% to 15% for different types of products as listed in the book Cosmetic Science and Technology by Edward Sagarin, Interscience Publishers 1957. The hydrogel fibers may be efficiently utilized as low as 1% due to their high swelling and storage properties. In fact, P-HEMA fibers may absorb proteinous materials and will adhere to cells—this may promote rapid ingrowth of cells and capillaries when applied to tissue mass for long periods of time.

P-HEMA fibers have been produced with spinerettes and by extrusion. For the following examples, we have used hollow fibers produced by extrusion having an outside diameter of 20 microns, a diameter of 10 microns and approximate wall thickness of 5 microns. They were then chopped into lengths of approximately 20 microns. The P-HEMA hollow fibers will act as a reservoir and matrix for diffusion-controlled delivery to skin and nails. P-HEMA fibers are combined with water along with active ingredients, humectant, protein or ethyl alcohol containing perfume and other ingredients required to be applied to skin and allowed to be absorbed. P-HEMA will absorb approximately 28% to 80% hydrophilic and hydrophobic fluids. The water content will vary from about 61.1% at osmotic equilibrium to about 74.5% at osmotic equilibrium.

EXAMPLE 1

| Lipstick Composition | |
| --- | --- |
| Carnauba Wax | 10% |
| Beeswax | 15% |
| Cetyl Alcohol | 5% |
| Ethyl Alcohol | 2% |
| Water | 2% |
| Protein Hydrolysate | 2% |
| Castor oil | 57% |
| P-HEMA-Methacrylate Copolymer Fiber | 7% |

Appropriate amount of dispersed color and perfume to be blended into above wax base at 80° C.

P-HEMA fibers, is dispersed into above base creating an excellent moisturizing lipstick composition.

LIQUID MAKE-UP

EXAMPLE 2

| Oil Phase | |
| --- | --- |
| Stearic Acid | 2.0 |
| Propylparaben | 0.1 |
| Mineral Oil | 10.0 |
| Glycerylmonostearate | 2.0 |
| Landin | 1.0 |
| Powder Phase | |
| Titanium Dioxide | 7.0 |
| Talc | 7.0 |
| Inorganic Color | 1.0 |
| P-HEMA | 5.0 |
| Water Base | |
| Water | 60.5 |
| Methylparaben | 0.15 |
| Triethanolamine | 1.00 |
| Propylene Glycol | 3.00 |
| Sodium Carboxymethyl Cellulose | .25 |

A. Add water base at 85° C. to oil phase at 85° C. while stirring; continue mixing while cooling to 30° C.; add powder blend in increments; mixing well after each addition.

EXAMPLE 3

| Face Powder | |
| --- | --- |
| P-HEMA (90%) - Vinyl Pyrolidone (10%) | 2 |
| Titanium Oxide | 10 |
| Talc | 68 |
| Zinc Stearate | 5 |
| Magnesium Carbonate | 2 |
| Precipitated Chalk | 3 |
| Kaolin | 10 |
| Color & Perfume, q.s. | |

EXAMPLE 4

| Nail Polish | |
| --- | --- |
| Nitrocellulose ½ sec. | 15.5 |
| Alcohol Anhydrous | 8.3 |
| Santolite Resin | 7.4 |
| Camphor | 2.5 |
| Dibutylphthalate | 5.0 |
| n-Butylacetate | 26.9 |
| Ethyl Acetate | 8.0 |
| Toluene | 25.4 |
| P-HEMA | 1.0 |

EXAMPLE 5

| Mascara | |
| --- | --- |
| Oleic Acid | 4.75 |
| Glyceryl Monostearate | 1.25 |
| Beeswax, Yellow | 9.0 |
| Carnauba Wax | 6.5 |
| Cellosize (H.V.) | 1.5 |
| Pigments | 5–8.0 |
| Triethanol Amine | 2.5 |
| Preservative q.s. | |
| Antioxidant q.s. | |
| P-HEMA | 8 |
| Water q.s. | |

EXAMPLE 6

| Nail Polish | |
| --- | --- |
| Nitrogeneous adduct of caboxymethyl cellulose using polyelectrolyte surfactant complexes | 16.5 |
| Alcohol Anhydrous | 8.3 |
| Santolite Resin | 7.4 |
| Camphor | 2.5 |
| Dibutylphthalata | 5.0 |
| n-Butylacetate | 26.9 |
| Ethyl Acetate | 8.0 |
| Toluene | 25.4 |

I claim:

1. A lipstick composition consisting of (a)polyHema fibers or copolymer of polyHema fibers wherein the monomer is selected from the group consisting of acrylic acid, methacrylic acid, crotonic acid, hydroxyethylmethacrylate, hydroxyethylacrylate, hydroxypropylacrylate, hydroxypropyl methacrylate, hydroxybutyl methacrylate, N-Vinyl-2-Pyrolidone, and neopentyl glycol dimethacrylate in a weight ratio of 0.5 to 15% of weight

| | | |
| --- | --- | --- |
| b. | Carnauba wax | 10% |
| c. | Beeswax | 15% |
| d. | Cetyl Alcohol | 5% |
| e. | Ethyl Alcohol | 2% |
| f. | Water | 2% |
| g. | Protein Hydrolysate | 2% |
| h. | Castor Oil | 57%. |

2. A liquid make-up composition comprising:
I. A Powder Phase Consisting of:
   a. PolyHema fibers or compolymer of polyHema fibers wherein the monomer is selected from the group consisting of acrylic acid, methacrylic acid, crotonic acid, hydroxyethylmethacrylate, hydroxyethylacrylate, hydroxypropylacrylate, hydroxypropyl methacrylate, hydroxybutyl methacrylate, N-Vinyl-2-Pyrolidone, and neopentyl glycol dimethacrylate in a weight ratio of 0.5 to 15% of weight

| | | |
|---|---|---|
| b. | Titanium Dioxide | 7.0% |
| c. | Talc | 7.0% |
| d. | Inorganic Color | 1.0% |

II. An Oil Phase Consisting of:

| | | |
|---|---|---|
| e. | Stearic Acid | 2.0% |
| f. | Propylparaben | 0.1% |
| g. | Mineral Oil | 10.0% |
| h. | Glyceryl Monostearate | 2.0% |
| i. | Landin | 1.0% |

III. And a Water Phase Consisting of:

| | | |
|---|---|---|
| j. | Water | 60.5% |
| k. | Methyl paraben | 0.15% |
| l. | Triethanolamine | 1.0% |
| m. | Propylene Glycol | 3.0% |
| n. | Sodium Carboxymethyl Cellulose | 0.25%. |

3. A Face Powder Composition Consisting of:
a. Polyhema fibers or copolymer of polyHema fibers wherein the monomer is selected from the group consisting of acrylic acid; methacrylic acid, crotonic acid, hydroxyethylmethacrylate, hydroxyethyl acrylate, hydroxypropylacrylate, hydroxypropyl methacrylate, hydroxybutyl methacrylate, N-Vinyl-2-Pyrolidone, and neopentyl glycol dimethacrylate in a weight ratio of 0.5 to 15% of weight

| | | |
|---|---|---|
| b. | Titanium Dioxide | 10% |
| c. | Talc | 68% |
| d. | Zinc Stearate | 5% |
| e. | Magnesium Carbonate | 2% |
| f. | Precipitated Chalk | 3% |
| g. | Kaolin | 10% |
| h. | Color and Perfume q.s. | |

4. A Nail Polish Composition Consisting of:
a. Polyhema Fibers or copolymer of polyHema fibers wherein the monomer is selected from the group consisting of acrylic acid, methacrylic acid, crotonic acid, hydroxyethylmethacrylate, hydroxyethyl acrylate, hydroxypropylacrylate, hydroxypropyl methacrylate, hydroxybutyl methacrylate, N-Vinyl-2-Pyrolidone, and neopentyl glycol dimethacrylate in a weight ratio of 0.5 to 15% of weight

| | | |
|---|---|---|
| b. | Nitrocellulose ½ sec. | 15.5% |
| c. | Alcohol Anhydrous | 8.3% |
| d. | Santolite Resin | 7.4% |
| e. | Camphor | 2.5% |
| f. | Dibutylphthalate | 5.0% |
| g. | n-Butylacetate | 26.9% |
| h. | Etthyl Acetate | 8.0% |
| i. | Toluene | 25.4%. |

5. A Mascara Composition Consisting of:
a. Polyhema fibers or copolymer of polyHema fibers wherein the monomer is selected from the group consisting of acrylic acid, methacrylic acid, crotonic acid, hydroxyethylmethacrylate, hydroxyethyl acrylate, hydroxypropylacrylate, hydroxypropyl methacrylate, hydroxybutyl methacrylate, N-Vinyl-2-Pyrolidone, and neopentyl glycol dimethacrylate in a weight ratio of 0.5 to 15% of weight

| | | |
|---|---|---|
| b. | Oleic Acid | 4.75% |
| c. | Glyceryl Monostearate | 1.25% |
| d. | Beeswax, Yellow | 8.0% |
| e. | Carnauba Wax | 6.5% |
| f. | Cellulose (H.V.) | 1.5% |
| g. | Pigments | 5–8% |
| h. | Triethanol Amine | 2.5% |
| i. | Preservative q.s. | |
| j. | Antioxidant q.s. | |
| k. | Water q.s. | |

\* \* \* \* \*